United States Patent
Bandy et al.

(10) Patent No.: US 9,581,532 B2
(45) Date of Patent: Feb. 28, 2017

(54) SUBSTRATE EDGE CLAMPING FORCE TESTER

(71) Applicant: INTERNATIONAL BUSINESS MACHINES CORPORATION, Armonk, NY (US)

(72) Inventors: John J. Bandy, Cambridge, VT (US); Bradley M. Mahan, Burlington, VT (US); Ralph W. Stevens, Jr., Milton, NY (US); Tracy A. Tong, Wallkill, NY (US)

(73) Assignee: International Business Machines Corporation, Armonk, NY (US)

( * ) Notice: Subject to any disclaimer, the term of this patent is extended or adjusted under 35 U.S.C. 154(b) by 260 days.

(21) Appl. No.: 14/558,804

(22) Filed: Dec. 3, 2014

(65) Prior Publication Data

US 2016/0161381 A1 Jun. 9, 2016

(51) Int. Cl.
*G01N 3/08* (2006.01)
*G01N 3/12* (2006.01)
*G01L 5/00* (2006.01)

(52) U.S. Cl.
CPC ............. *G01N 3/12* (2013.01); *G01L 5/0061* (2013.01)

(58) Field of Classification Search
CPC ............................................. G01N 2203/0411
USPC ............................ 73/857, 856, 837, 862.583
See application file for complete search history.

(56) References Cited

U.S. PATENT DOCUMENTS

| | | |
|---|---|---|
| 5,350,427 A | 9/1994 | Freytsis et al. |
| 6,498,047 B2 | 12/2002 | Kim et al. |
| 7,194,917 B2 | 3/2007 | Dung |
| 7,700,379 B2 | 4/2010 | Haji-Sheikh et al. |
| 8,310,682 B2 | 11/2012 | Orthner et al. |

FOREIGN PATENT DOCUMENTS

CN 103308100 9/2013

*Primary Examiner* — David Gray
*Assistant Examiner* — Andrew V Do
(74) *Attorney, Agent, or Firm* — Schmeiser, Olsen & Watts; Steven Meyers

(57) ABSTRACT

An apparatus and methods for measuring the clamping force applied to a substrate by clamping elements of a substrate holder. The apparatus include a pneumatic cylinder, a two position, three way valve and a pressure gauge. In a first position of the valve, the gauge and a bore of the cylinder are vented or pre-pressurized. In a second position of the valve, the bore and gauge are isolated. The methods include placing the apparatus with the valve in the first position between clamping elements set to a non-clamping position, moving the valve to the second position, setting the clamping elements to a clamping position and reading a pressure on the gauge.

20 Claims, 4 Drawing Sheets

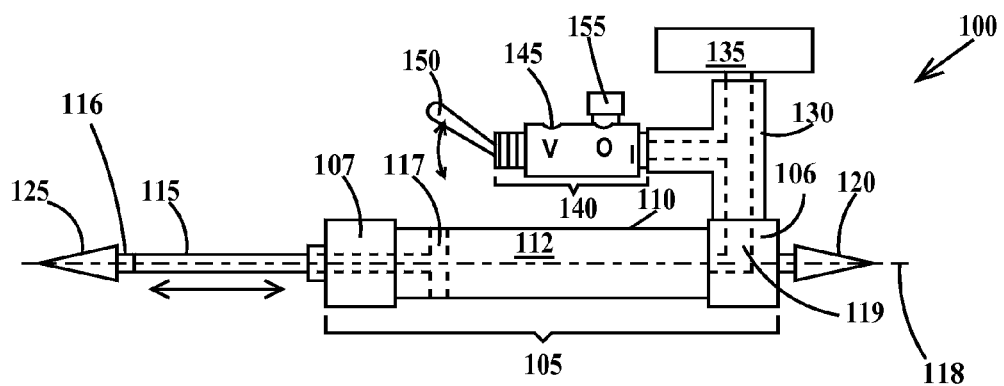
FIG. 1A
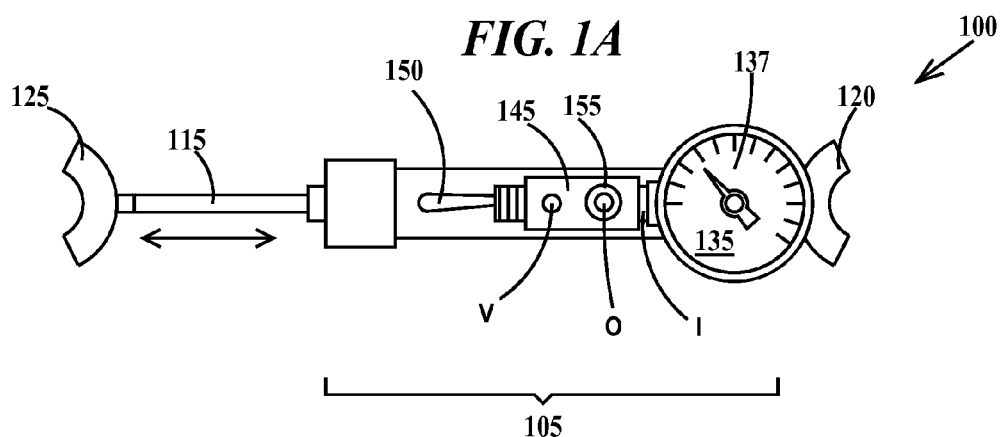
FIG. 1B
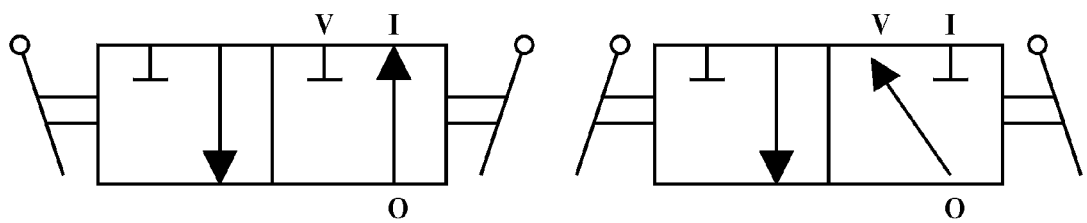
FIG. 2A  FIG. 2B

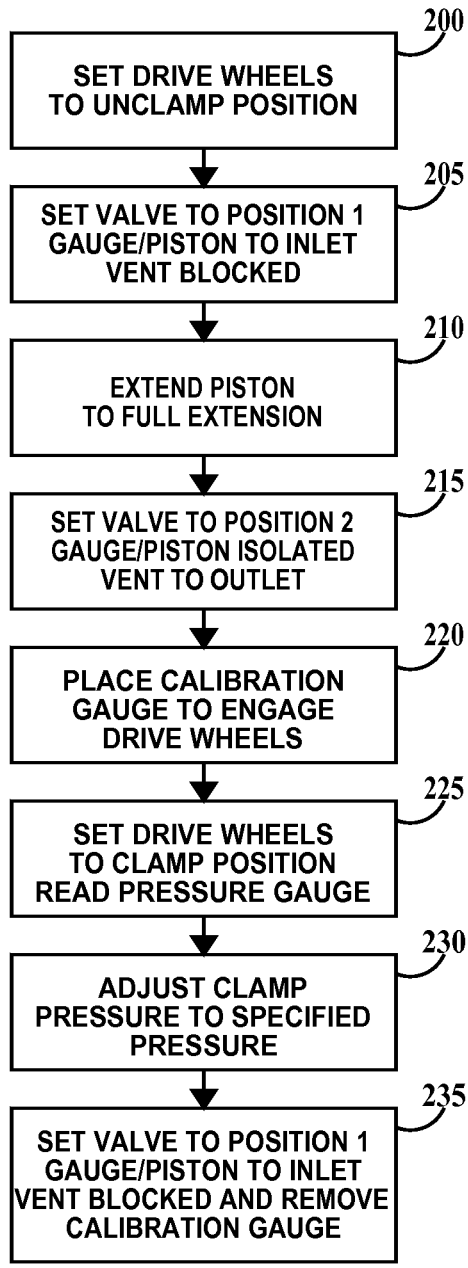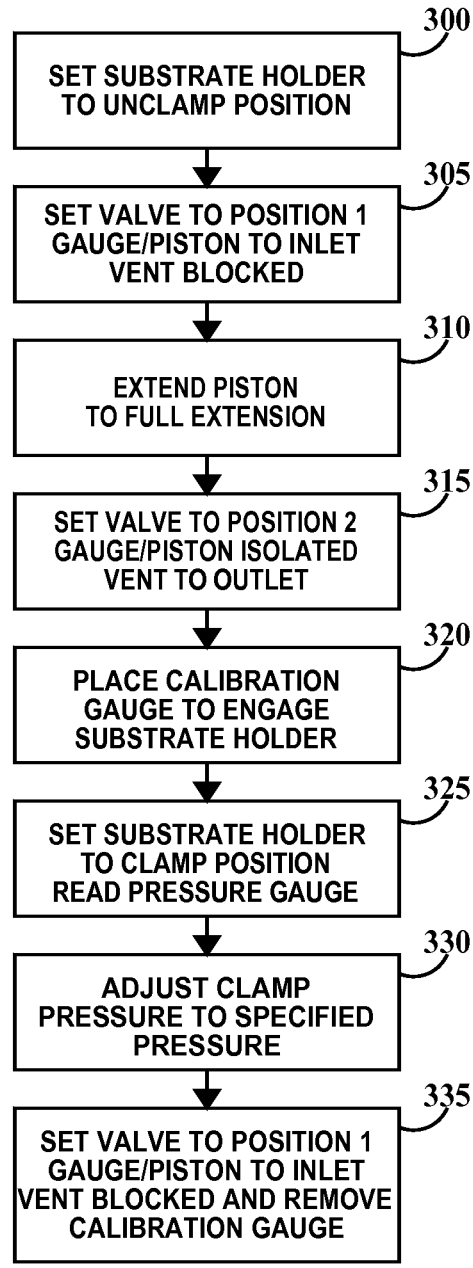
*FIG. 5*  *FIG. 6*

SUBSTRATE EDGE CLAMPING FORCE TESTER

BACKGROUND

The present invention relates to the field of integrated circuit manufacture; more specifically, it relates to an apparatus and method for directly measuring the clamping force on the edge of a substrate on a tool that applies clamping force pneumatically using a remote pressure regulator.

Many fabrication tools handle the substrate being processed by clamping the edges of the substrate. Generally the clamping force is applied pneumatically using a pressure regulator and gauges that are remotely located from the actual point where the substrate is contacted. Being remote the pressure set by a pressure regulator and indicated on the gauges is not the same as the pressure actually applied to the substrate edge because of friction in the shafts and bearings of the tool and pressure drops in the pneumatic system of the tool making it difficult to accurately calculate the actual force applied by the clamping mechanism. In certain tools, the clamping force can affect the quality and repeatability of the process or result in substrate damage.

Accordingly, there exists a need in the art to mitigate the deficiencies and limitations described hereinabove.

BRIEF SUMMARY

A first aspect of the present invention is an apparatus, comprising: a pneumatic cylinder having opposite first and second ends and having a bore having a longitudinal axis, a piston within the bore connected to a piston rod, the piston free to slide along the longitudinal axis within the bore, the piston rod extendable from the first end of the pneumatic cylinder, a gas port communicating with the bore in the second end of the pneumatic cylinder; a two-position three way valve having a vent, an outlet and an inlet, the inlet connected to the gas port and to a pressure gauge, in a first position of the valve the outlet connected to the inlet and the vent is not connected to the outlet or the inlet, and in a second position of the valve the outlet is connected to the vent and the inlet is not connected to the vent or the inlet; a pressure gauge connected to the inlet and connected to the bore through the gas port; and a first adapter connected to the second end of the pneumatic cylinder and a second adapter connected to an external end of the piston rod, the first and second adapters configured to engage clamping elements of a substrate holder configured to edgewise engage a substrate.

A second aspect of the present invention is a method comprising: providing a tool having clamping elements of a substrate holder configured to edgewise engage a substrate; providing a clamping force tester comprising a pneumatic cylinder having a piston slideably engaged in a bore and connected to a two way three position valve and to a pressure gauge, a first adapter connected to an end of the pneumatic cylinder opposite the piston rod and a second adapter connected to the piston rod, the first and second adapters configured to engage clamping elements of a substrate holder configured to edgewise engage a substrate; setting the clamping elements to a non-clamping position; setting the two way three position valve to a first position wherein the pressure gauge and the bore are open to ambient atmosphere; fully extending the piston rod from the pneumatic cylinder; setting the two way three position valve to a second position wherein the bore and the pressure gauge are isolated and wherein movement of the piston rod into the bore increases the pressure in the bore to a pressure greater than ambient atmospheric pressure; placing the clamping force tester between the clamping elements; setting the clamping elements to a clamping position; reading the pressure on the pressure gauge; and setting the two way three position valve to the first position and removing clamping force tester from the tool.

A third aspect of the present invention is a method comprising: providing a tool having clamping elements of a substrate holder configured to edgewise engage a substrate; providing a clamping force tester comprising a pneumatic cylinder having a piston slideably engaged in a bore and connected to a two way three position valve and to a pressure gauge, a first adapter connected to an end of the pneumatic cylinder opposite the piston rod and a second adapter connected to the piston rod, the first and second adapters configured to engage clamping elements of a substrate holder configured to edgewise engage a substrate; setting the clamping elements to a non-clamping position; setting the two way three position valve to a first position wherein the pressure gauge and the bore are connected to a precharge line pressurized to a precharge pressure that is greater than ambient atmospheric pressure; fully extending the piston rod from the pneumatic cylinder if not fully extended by the precharge pressure; setting the two way three position valve to a second position wherein the bore and the pressure gauge are isolated from the precharge pressure and wherein movement of the piston rod into the bore increases the pressure in the bore to a pressure greater than the precharge pressure; placing the clamping force tester between the clamping elements; setting the clamping elements to a clamping position; reading the pressure on the pressure gauge; and setting the two way three position valve to the first position and removing clamping force tester from the tool.

These and other aspects of the invention are described below.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings, wherein:

FIG. 1A is a top view and FIG. 1B is a side view of a substrate edge clamping force tester according to embodiments of the present invention;

FIG. 2A a schematic diagram of the poppet valve of FIGS. 1A and 1B in a first position and FIG. 2B a schematic diagram of the poppet valve of FIGS. 1A and 1B in a second position;

FIG. 5 is a flowchart of a method of measuring the clamping force applied to a substrate illustrated in FIGS. 4A and 4B; and FIG. 6 is a flowchart of a generic method of measuring the clamping force applied to a substrate by a tool.

DETAILED DESCRIPTION

Figure 3A:
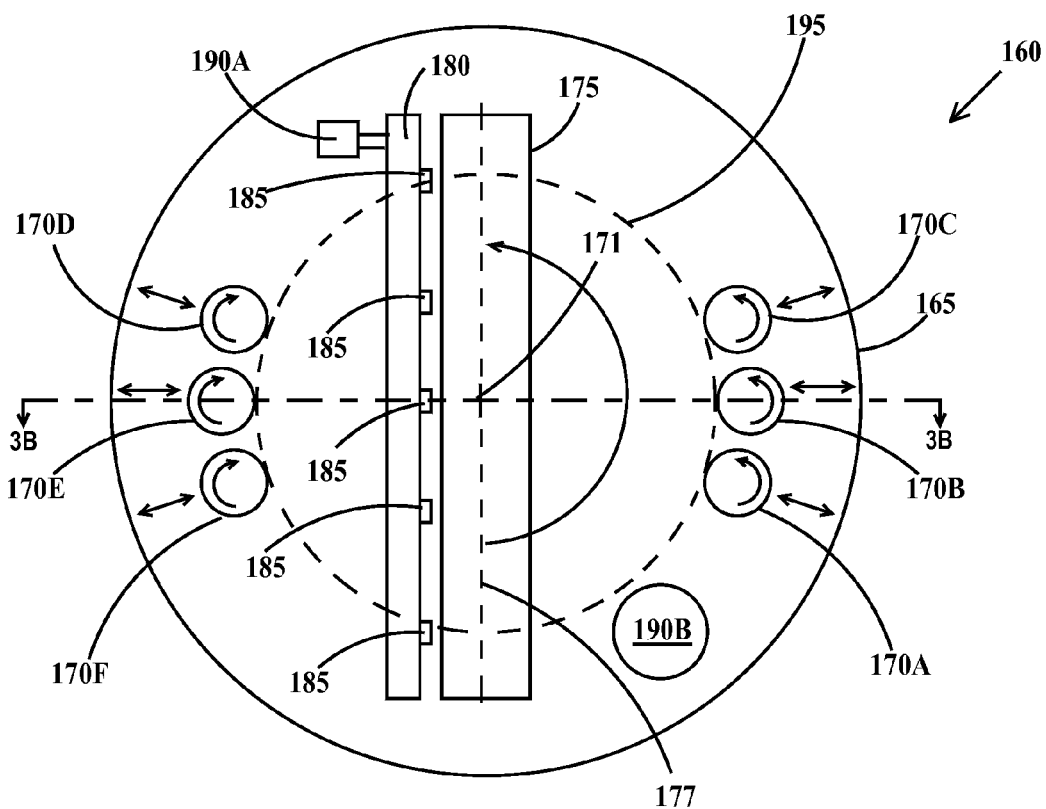
FIG. 3A is top view and FIG. 3B is a side view through line 3B-3B of FIG. 3A of a brush cleaning tool according to an embodiment of the present invention.

The embodiments of the present invention will be illustrated using a roller brush cleaner for cleaning the top surface of semiconductor wafers (a specific example of a substrate) after a chemical-mechanical-polish (CMP) process, though the apparatus may be adapted to other tools. A roller brush cleaner applies clamping pressure to the edges of a wafer via rotatable wheels attached to rotation assemblies. The wheels both clamp and rotate the wafer. Clamping is performed using pneumatics to force the rotation assemblies (and thus the wheels) toward the edges of the wafer. The amount of force is set by a pressure regulator having gauges for measuring the regulator output pressure that is remotely located (there are pneumatic lines between the rotation assemblies and the regulator).

A substrate edge clamping force tester (which is not part of the roller brush cleaner) according to embodiments of the present invention is placed between the wheels in lieu of the wafer and measures the pressure (the force is easily calculated) that the wheels directly apply to the edge clamping force tester and would directly apply to the wafer.

FIG. 1A is a top view and FIG. 1B is a side view of a substrate edge clamping force tester according to embodiments of the present invention. In FIGS. 1A and 1B, a clamping force tester 100 includes a pneumatic cylinder 105 having opposite first and second ends 106 and 107. Pneumatic cylinder 105 includes a body 110 having a bore 112 and a piston rod 115 having an external end 116 outside of bore 112 and a piston 117 within bore 112. Piston 117 is free to slide within bore 112. Piston rod 115 and bore 112 share a common longitudinal axis 118. Piston rod 115 is slideably engaged in bore 112 and can retract into and extend out of bore 115 along the common longitudinal axis 118. A gas port 119 is contained within second end 119. A first adapter 120 is attached to the first end 106 of pneumatic cylinder 105 and a second adapter 125 is attached to external end 116 of piston rod 115. Adapters 120 and 125 are configured to allow attachment of clamping force tester to the elements of a tool that engages the edges of substrates.

A hollow "Tee" connector 130 has a first end connected to first end 106 of pneumatic cylinder, a second end connected to a pressure gauge 135 and a third end connected a valve 140. The dashed lines show that "Tee" connector 130 allows communication between bore 112, pressure gauge 135 and an inlet I of valve 140.

Valve 140 is a two position three way valve. In the example of FIGS. 1A and 1B, valve 140 is two position poppet valve. A poppet valve is convenient in that it has a small form fact and is easily switched in tight spaces. Alternatively, valve 140 may be a two position three way rotary ball valve, a two position three way rotary cylinder valve or a two position three way slide valve. Valve 140 includes a body 145 having an inlet I which is connected to "Tee" 130, an outlet O and a vent 145. The internal connections between vent V, outlet O and inlet I is controlled by toggle 150 which has an up position and a down position. An optional fitting 155 is threaded into outlet O to allow attachment of an optional pre-charge gas line (not shown). Examples of pre-charge gas include air and nitrogen. Vent V is open to ambient atmosphere and outlet O is open to ambient atmosphere unless it is connected to a pre-charge gas line.

FIG. 2A a schematic diagram of the poppet valve of FIGS. 1A and 1B in a first position and FIG. 2B a schematic diagram of the poppet valve of FIGS. 1A and 1B in a second position. In the first position (FIG. 2A), the outlet O is connected to inlet I, and vent V is blocked (not connected to either inlet I or outlet O). In FIG. 1A, the first position connects bore 112 and pressure gauge 135 to outlet O and vent V is not connected to outlet O, bore 112 or pressure gauge 135. The first position opens bore 112 and pressure gauge 135 to ambient atmospheric pressure (or to a precharge line). In the second position (FIG. 2B), the outlet O is connected to vent V, and inlet I is blocked (not connected to either vent V or outlet O). In FIG. 1B, the second position connects bore 112 and pressure gauge 135 to vent I and vent V is not connected to outlet O, inlet I, bore 112 or pressure gauge 135. The second position seals bore 112 and pressure gauge 135 from the ambient atmospheric pressure allowing pressure to increase as piston rod 115 is forced into bore 112.

Figure 3B:
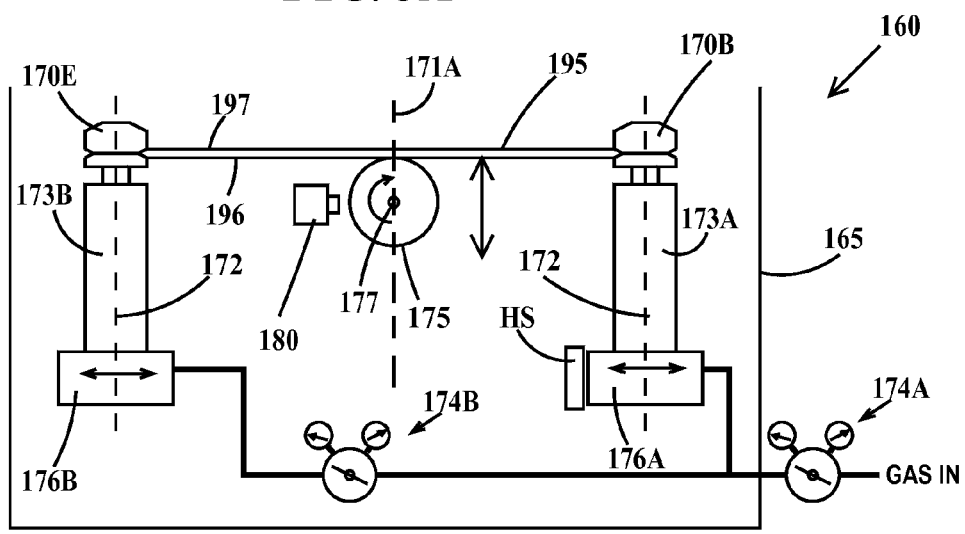

FIG. 3A is top view and FIG. 3B is a side view through line 3B-3B of FIG. 3A of a brush cleaning tool according to an embodiment of the present invention. In FIGS. 3A and 3B a roller brush clean 160 includes an enclosure 165 and six drive wheels 170A, 170B, 170C, 170D, 170E and 170F radially arranged about a central point 171. Centers of each of the drive wheels 170A, 170B, 170C, 170D, 170E and 170F are positioned the same distance from central point 171. Drive wheels 170A, 170B and 170C are arranged on a right side of central point 171 and drive wheels 170D, 170E and 170F are arranged on a left side of point 171. Drive wheel 170B is positioned between and equally distant from drive wheels 170A and 170C. Drive wheel 170E is positioned between and equally distant from drive wheels 170D and 170F. Drive wheels 170A, 170B and 170C are arranged symmetrically to drive wheels 170D, 170E and 170F. Drive wheels 170A, 170B, 170C, 170D, 170E and 170F are free to rotate about respective axes 172. Axes 172 are perpendicular to top surface 196 of wafer 195. Drive wheels 170A, 170B and 170C are supported by respective roller pillars 173A also aligned along respective axes 172. Drive wheels 170D, 170E and 170F are supported by respective drive cylinders 173B. The three roller pillars 173A are mounted to a clamping cylinder 176A and the three roller pillars 173B are mounted to a clamping cylinder 176B which enable roller pillars 173A and 173B to move in concert and can move toward or away from a vertical axis 171A extending from central point 171. Drive pillars 173A move along radii extending from vertical axis 171A and are driven by clamping cylinder 176A which is activated by gas supplied from regulator 174A while their respective axes 172 remain perpendicular to top surface 196 of wafer 195. Similarly drive pillars 173B move along radii extending from vertical axis 171A and are driven by clamping cylinder 176B which is activated by gas supplied from regulator 174B while their respective axes 172 remain perpendicular to top surface 196 of wafer 195. When pneumatic system 174 moves drive cylinders 173 inward, drive wheels 170A, 170B, 170C, 170D, 170E and 170F exert clamping force on wafer 195. The amount of force exerted on wafer 195 is set by pressure regulators 174B because of the hard stop HS which limits the inward travel of clamping cylinder 176A. Hard stop HS is adjustable and allows centering of wafer 195 to axis 171A. When drive wheels 170A, 170B, 170C, 170D, 170E and 170F rotate they exert rotational force on wafer 195.

In one example, wheels 170A, 170B and 170C rotate in a counter clockwise direction and wheels 170D, 170E and 170CF rotate in a clockwise direction forcing wafer 171 to rotate in a counterclockwise direction.

A roller brush 175 having a longitudinal axis 177 is positioned under central point 171. Longitudinal axis 177 is perpendicular to a line passing through the centers of wheels 170B and 170E. Roller brush 175 is rotatable about longitudinal axis 177. Positioned parallel to one side of roller brush 175 is a manifold 180 having a series of spray nozzles 185. Manifold 180 includes a cleaning fluid supply port 190A for supplying cleaning fluid (e.g., water) to manifold 180. Enclosure 165 includes a drain 190B. A wafer 195 (dashed lines) having a top surface 196 and a bottom surface 197 is illustrated engaged by drive wheels 170A, 170B, 170C, 170D, 170E and 170F so the center of the wafer is aligned directly under central point 171. Roller brush 175 is illustrated contacting top surface 196. Top surface 196 is the surface where integrated circuit chips are fabricated. Longitudinal axis 177 is parallel to top surface 196 of wafer 195. Brush roller 175 and manifold 185 are movable toward and away from wafer 195.

In operation, wafer 195 is positioned top surface 196 down between drive wheels 170A, 170B, 170C, 170D, 170E and 170F (the drive wheels are in the dis-engage or non-clamping position) by a wafer handling system (not shown) and the clamping cylinders 176A and 176B are activated (moved inward) forcing drive wheels 170A, 170B, 170C, 170D, 170E and 170F to exert clamping force on wafer 196. Next drive wheels 170A, 170B, 170C, 170D, 170E and 170F are rotated thereby spinning wafer 195 about the center of wafer 195. Next, cleaning fluid is sprayed on to roller brush 175 through nozzles 185 and roller brush 175 is rotated. Next, roller brush 175 and manifold 180 are moved upward until roller brush 175 contacts the top surface 196 of wafer 195. Cleaning is performed for a pre-determined length of time. After cleaning is complete, the roller brush 175 is retracted, the cleaning fluid turned off, the wafer spinning is stopped, the wafer handling system is positioned to catch wafer 195 and clamping cylinders 1736A and 176B are deactivated (moved outward) thereby disengaging drive wheels 170A, 170B, 170C, 170D, 170E and 170F so as to no longer exert clamping force on wafer 195.

Figure 4A:
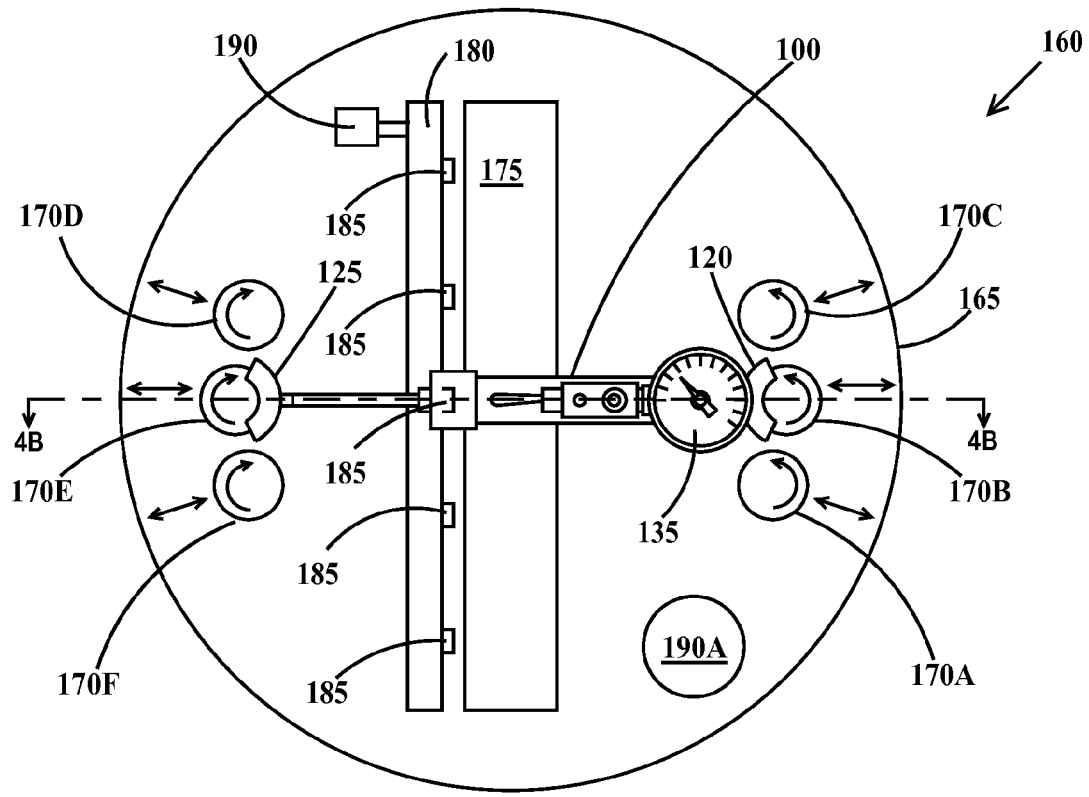
FIG. 4A is top view and FIG. 4B is a side view through line 4B-4B of FIG. 4A of the brush cleaning tool of FIGS. 3A and 3B with a substrate edge clamping force tester according to an embodiment of the present invention in place.
Figure 4B:
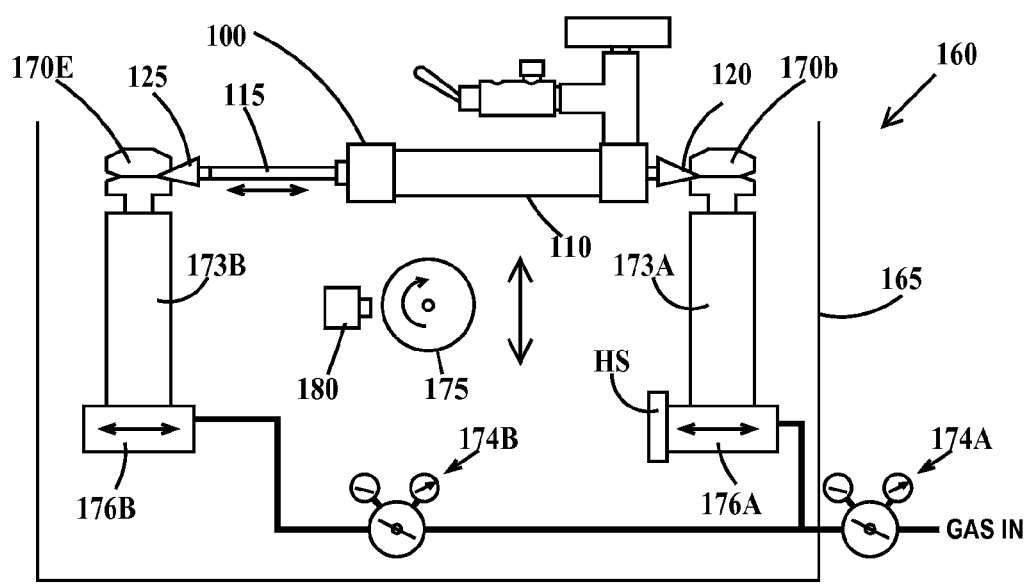

FIG. 4A is top view and FIG. 4B is a side view through line 4B-4B of FIG. 4A of the brush cleaning tool of FIGS. 3A and 3B with a substrate edge clamping force tester according to an embodiment of the present invention in place. In FIGS. 4A and 4B, clamping force detector 100 is positioned between drive rollers 170B and 170E with adapter 120 removeably engaging a groove in drive wheel 170B and adapter 125 removeably engaging a groove in drive wheel 170E. The length of clamping force tester with piston 115 fully extended is greater than the distance between drive wheels 170B and 170E in the non-clamping position. The drive wheels 170A, 170B, 170C, 170D, 170E and 170F are in the unclamped position. Piston rod 115 is in an extended (but not fully extended) position in order to accomplish this. There may be some preload pressure on gauge 135. The bore diameter of body 110 and length of stroke of piston rod 115 are design considerations based on tool clamp range of travel, clamping pressure range and any desired preload.

FIG. 5 is a flowchart of a method of measuring the clamping force applied to a substrate illustrated in FIGS. 4A and 4B. In step 200, the drive wheels of the brush cleaner are set to the non-clamped position. In step 205, the valve of the clamping force tester is set to its first position which connects the bore and pressure gauge to ambient atmospheric pressure or optionally to a precharge pressure supplied by a precharge line connected to the outlet of the two position three way valve. The precharge pressure is a pressure lower than the pressure expected to be read when the drive wheels are in the clamp position. For example, precharge pressure would be 5-6 psi when the clamping pressure is about 12 psi. In step 210, the piston is extended to its full extent if not already extended by precharge pressure. In step 215, the valve of the clamping force tester is set to its second position where the bore and pressure gauge are isolated from the ambient atmosphere (or from any precharge pressure). With no precharge, the pressure gauge will read 0 psi. Next, in step 220, the clamping force tester is placed into position between an opposite pair of drive wheels. The adapters of the clamping force tester engage the grooves of the drive wheels. In step 225, the drive wheels are set to the clamp position which would push the piston rod into the cylinder bore thereby increasing the pressure within the bore which can be read on the gauge. Pressure can be converted to force by multiplying the pressure read by the bore radius squared times pi. In step 230, the clamping pressure may be adjusted to a specified value, if so desired, using the pneumatic controls of the tool. Finally, in step 235, the valve is set to its first position, venting the gauge and bore to atmosphere (or to precharge pressure) and the clamping force tester is removed from the brush cleaner.

FIG. 6 is a flowchart of a generic method of measuring the clamping force applied to a substrate by substrate holder or a substrate holder included in a process tool. In step 300, the substrate holder of the tool is set to the non-clamped position. In step 305, the valve of the clamping force tester is set to its first position which connects the bore and pressure gauge to ambient atmospheric pressure or optionally to a precharge pressure supplied by a precharge line connected to the outlet of the two position three way valve. The precharge pressure is a pressure lower than the pressure expected to be read when the drive wheels are in the clamp position. In one example, the precharge pressure is half or less than the clamping pressure. In step 310, the piston is extended to its full extent if not already extended by precharge pressure. In step 315, the valve of the clamping force tester is set to its second position where the bore and pressure gauge are isolated from the ambient atmosphere (or from any precharge pressure). With no precharge, the pressure gauge will read 0 psi. Next, in step 320, the clamping force tester is placed into position between opposite clamping elements of the substrate holder. In step 325, the substrate holder is set to the clamp position which would push the piston rod into the cylinder bore thereby increasing the pressure within the bore which can be read on the gauge. In step 330, the clamping pressure may be adjusted to a specified value, if so desired, using the controls of the substrate holder. Finally, in step 335, the valve is set to its first position, venting the gauge and bore to atmosphere or to precharge pressure and the clamping force tester is removed from the substrate holder.

When the precharge pressure is low, the steps outlined supra and illustrated in FIGS. 5 and 6 are performed as discussed because manual insertion and removal of the clamping force tester does not require inordinate strength on the part of the operator. However, at high precharge pressures, the precharge line is not attached until after the clamping force tester is positioned between the drive wheels or clamping elements and removed before the clamping force tester is removed.

Thus the embodiments of the present invention provide an apparatus and method for directly measuring the clamping force on the edge of a substrate on a tool that applies clamping force pneumatically using a remote pressure regulator.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus, comprising:
a pneumatic cylinder having opposite first and second ends and having a bore having a longitudinal axis, a piston within said bore connected to a piston rod, said piston free to slide along said longitudinal axis within said bore, said piston rod extendable from said first end of said pneumatic cylinder, a gas port communicating with said bore in said second end of said pneumatic cylinder;
a two-position three way valve having a vent, an outlet and an inlet, said inlet connected to said gas port and to a pressure gauge, in a first position of said valve said outlet connected to said inlet and said vent is not connected to said outlet or said inlet, and in a second position of said valve said outlet is connected to said vent and said inlet is not connected to said vent or said inlet;
a pressure gauge connected to said inlet and connected to said bore through said gas port; and
a first adapter connected to said second end of said pneumatic cylinder and a second adapter connected to an external end of said piston rod, said first and second adapters configured to engage clamping elements of a substrate holder configured to edgewise engage a substrate.

2. The apparatus of claim 1, wherein in said first position of said valve said pressure gauge and said bore are open to ambient atmosphere and in said second position said bore and said pressure gauge are isolated and pressurized to ambient atmospheric pressure and wherein movement of said piston rod into said bore increases the pressure in said bore to a pressure greater than ambient atmospheric pressure.

3. The apparatus of claim 1, further including:
a pre-charge gas line at a precharge pressure that is greater than ambient atmospheric pressure; and
wherein in said first position of said valve said pressure gauge and said bore are connected to said pre-charge gas line and in said second position said bore and said pressure gauge are isolated and pressurized to said precharge pressure and wherein movement of said piston rod into said bore increases the pressure in said bore to a pressure greater than said precharge pressure.

4. The apparatus of claim 1, wherein said two position three way valve is selected from the group consisting of poppet valves, slide valves, a rotary ball valves and rotary cylinder valves.

5. The apparatus of claim 1, wherein in both said first and second positions of said two position three way valve said vent is connected to ambient atmospheric pressure.

6. The apparatus of claim 1, wherein said two way three position valve and said pressure gauge are mounted on a same side of said pneumatic cylinder with the dial face of said pressure gauge facing away from said pneumatic cylinder.

7. The apparatus of claim 1, wherein said first and second adapters are configured to engage opposite first and second rollers of a tool that applies clamping and rotational force the edges of a disk shaped substrate, said first and second rollers being said clamping elements of said substrate holder.

8. The apparatus of claim 7, wherein said tool is a brush cleaner and said disk-shaped substrate is a semiconductor substrate.

9. A method comprising:
providing a tool having clamping elements of a substrate holder configured to edgewise engage a substrate;
providing a clamping force tester comprising a pneumatic cylinder having a piston slideably engaged in a bore and connected to a two way three position valve and to a pressure gauge, a first adapter connected to an end of said pneumatic cylinder opposite said piston rod and a second adapter connected to said piston rod, said first and second adapters configured to engage clamping elements of a substrate holder configured to edgewise engage a substrate;
setting said clamping elements to a non-clamping position;
setting said two way three position valve to a first position wherein said pressure gauge and said bore are open to ambient atmosphere;
fully extending said piston rod from said pneumatic cylinder;
setting said two way three position valve to a second position wherein said bore and said pressure gauge are isolated and wherein movement of said piston rod into said bore increases the pressure in said bore to a pressure greater than ambient atmospheric pressure;
placing said clamping force tester between said clamping elements;
setting said clamping elements to a clamping position;
reading the pressure on said pressure gauge; and
setting said two way three position valve to said first position and removing clamping force tester from said tool.

10. The method of claim 9, wherein
said pneumatic cylinder having opposite first and second ends and said bore having a longitudinal axis, a piston within said bore connected to said piston rod, said piston free to slide along said longitudinal axis within said bore, said piston rod extendable from said first end of said pneumatic cylinder, a gas port communicating with said bore in said second end of said pneumatic cylinder;
said two-position three way valve having a vent, an outlet and an inlet, said inlet connected to said gas port and to a pressure gauge, in a first position of said valve said outlet connected to said inlet and said vent is not connected to said outlet or said inlet, and in a second position of said valve said outlet is connected to said vent and said inlet is not connected to said vent or said inlet; and
said pressure gauge connected to said inlet and connected to said bore through said gas port.

11. The method of claim 9, further including:
between reading said pressure gauge and removing said clamping force tester adjusting the clamping pressure of said substrate holder to a specified value.

12. The method of claim 9, wherein said two position three way valve is selected from the group consisting of poppet valves, slide valves, a rotary ball valves and rotary cylinder valves.

13. The method of claim 9, wherein in both said first and second positions of said two position three way valve said vent is connected to ambient atmospheric pressure.

14. The method of claim 9, wherein said two way three position valve and said pressure gauge are mounted on a same side of said pneumatic cylinder with the dial face of said pressure gauge facing away from said pneumatic cylinder.

15. The method of claim 9, wherein said first and second adapters are configured to engage opposite first and second rollers of a tool that applies clamping and rotational force the edges of a disk shaped substrate, said first and second rollers being said clamping elements of said substrate holder.

16. The method of claim 15, wherein said tool is a brush cleaner and said disk-shaped substrate is a semiconductor substrate.

17. The method of claim 9, wherein said first and second adapters are configured to engage opposite first and second rollers of a tool that applies clamping and rotational force the edges of a disk shaped substrate, said first and second rollers being said clamping elements of said substrate holder.

18. A method comprising:
providing a tool having clamping elements of a substrate holder configured to edgewise engage a substrate;
providing a clamping force tester comprising a pneumatic cylinder having a piston slideably engaged in a bore and connected to a two way three position valve and to a pressure gauge, a first adapter connected to an end of said pneumatic cylinder opposite said piston rod and a second adapter connected to said piston rod, said first and second adapters configured to engage clamping elements of a substrate holder configured to edgewise engage a substrate;
setting said clamping elements to a non-clamping position;
setting said two way three position valve to a first position wherein said pressure gauge and said bore are connected to a precharge line pressurized to a precharge pressure that is greater than ambient atmospheric pressure;
fully extending said piston rod from said pneumatic cylinder if not fully extended by said precharge pressure;
setting said two way three position valve to a second position wherein said bore and said pressure gauge are isolated from said precharge pressure and wherein movement of said piston rod into said bore increases the pressure in said bore to a pressure greater than said precharge pressure;
placing said clamping force tester between said clamping elements;
setting said clamping elements to a clamping position;
reading the pressure on said pressure gauge; and
setting said two way three position valve to said first position and removing clamping force tester from said tool.

19. The method of claim 18, wherein
said pneumatic cylinder having opposite first and second ends and said bore having a longitudinal axis, a piston within said bore connected to said piston rod, said piston free to slide along said longitudinal axis within said bore, said piston rod extendable from said first end of said pneumatic cylinder, a gas port communicating with said bore in said second end of said pneumatic cylinder;
said two-position three way valve having a vent, an outlet and an inlet, said inlet connectable to a precharge line at a precharge pressure, said inlet connected to said gas port and to a pressure gauge, in a first position of said valve said outlet connected to said inlet and said vent is not connected to said outlet or said inlet, and in a second position of said valve said outlet is connected to said vent and said inlet is not connected to said vent or said inlet; and
said pressure gauge connected to said inlet and connected to said bore through said gas port.

20. The method of claim 18, further including:
between reading said pressure gauge and removing said clamping force tester adjusting the clamping pressure of said substrate holder to a specified value.

* * * * *